US00PP33938P2

(12) United States Plant Patent
Randag

(10) Patent No.: US PP33,938 P2
(45) Date of Patent: Feb. 1, 2022

(54) CALLA LILY PLANT NAMED 'DOZANTOKY'

(50) Latin Name: *Zantedeschia sprengeri*
Varietal Denomination: Dozantoky

(71) Applicant: Dümmen Group B.V., De Lier (NL)

(72) Inventor: Cecilius Jan-Jochem Randag, Koedijk (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/307,210

(22) Filed: May 4, 2021

(51) Int. Cl.
*A01H 5/02* (2018.01)
*A01H 6/10* (2018.01)

(52) U.S. Cl.
USPC ..... Plt./490

(58) Field of Classification Search
USPC ..... Plt./490

CPC ... A01H 5/02; A01H 5/00; A01H 6/10; A01H 6/56
See application file for complete search history.

(56) References Cited

PUBLICATIONS

CS Weijers, retrieved on Jul. 22, 2021, retrieved from the Internet at https://translate.google.com/translate?hl=en&sl=nl&tl=en&u=https%3A%2F%2Fwww.csweijers.nl%2Fassortiment%2Fzantedeschia&prev=search, 5 pp. (Year: 2021).*
Visions Pictures retrieved on Jul. 22, 2021, retrieved from the Internet at https://www.visionspictures.com/en/asset/421451_zantedeschia-tokyo, one page. (Year: 2021).*

* cited by examiner

*Primary Examiner* — June Hwu
(74) *Attorney, Agent, or Firm* — The Webb Law Firm

(57) ABSTRACT

'Dozantoky' is a new variety of calla lily plant having reddish purple colored spathes that produces 5-10 inflorescences per 16-18 cm tuber. The flower stems are about 22-25 cm in height. The leaves are deep green with maculations present and a smooth texture.

2 Drawing Sheets

Botanical classification: *Zantedeschia sprengeri*.
Varietal denomination: 'Dozantoky'.

BACKGROUND OF THE NEW PLANT

The present invention comprises a new and distinct variety of calla lily, botanically known as *Zantedeschia sprengeri* and hereinafter referred to by the varietal name 'Dozantoky'. 'Dozantoky' is a product of a planned breeding program, which had the objective of creating *Zantedeschia* hybrids for pot flower production in a wide range of colors with a classic flower shape. The new cultivar is a seedling selected from the crossing of *Zantedeschia sprengeri* seedling Z061138-9104 (female parent, unpatented) with *Zantedeschia sprengeri* variety 'Zazu' (male parent, U.S. Plant Pat. No. 28,164). 'Dozantoky' was selected in 2014 by the inventor in 't Zand, The Netherlands as one flowering plant within the progeny of the stated cross.

The first act of asexual reproduction of 'Dozantoky' by tissue culture was performed by the inventor in November of 2014 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants at approximately 11 weeks from planting in 14 cm pots in 't Zand, The Netherlands under greenhouse conditions, which approximate those generally used in horticultural practice. Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Dozantoky' which, in combination, distinguish this calla lily as a new and distinct cultivar:

1. Medium reddish purple colored spathes with a violet colored throat spot;
2. Deep green colored leaves; and
3. Few to an average number leaf maculations present.

The new variety is similar to its female parent in the following traits: spathe and stem color, spathe width, weak flower curve, and the presence of leaf maculations. However, 'Dozantoky' exhibits a shorter spathe length and a longer spadix length than its female parent. Further, its female parent does not have a spathe throat spot and has oval shaped leaves. The new variety is similar to its male parent in the following traits: violet colored spathe throat spot, spathe width, spadix length, lanceolate leaf shape, and the presence of leaf maculations. However, 'Dozantoky' exhibits a shorter spathe length and a later flowering time than its male parent. Further, its male parent h.as pink colored spathes and green stems.

When compared to calla lily plant named 'Samur' (unpatented—abandoned U.S. Plant patent application Ser. No. 13/374,316), 'Samur' has an upper surface spathe color from Red-Purple Group RHS 68B to 68D, whereas the upper surface spathe color of 'Dozantoky' is from Red-Purple Group RHS 59B to 59C.

BRIEF DESCRIPTION OF THE DRAWINGS

The accompanying photographic drawings illustrate the new variety taken at approximately 11 weeks of age, with the colors being as nearly true as is possible with color illustrations of this type.

DESCRIPTION OF THE NEW PLANT

Figure 1:
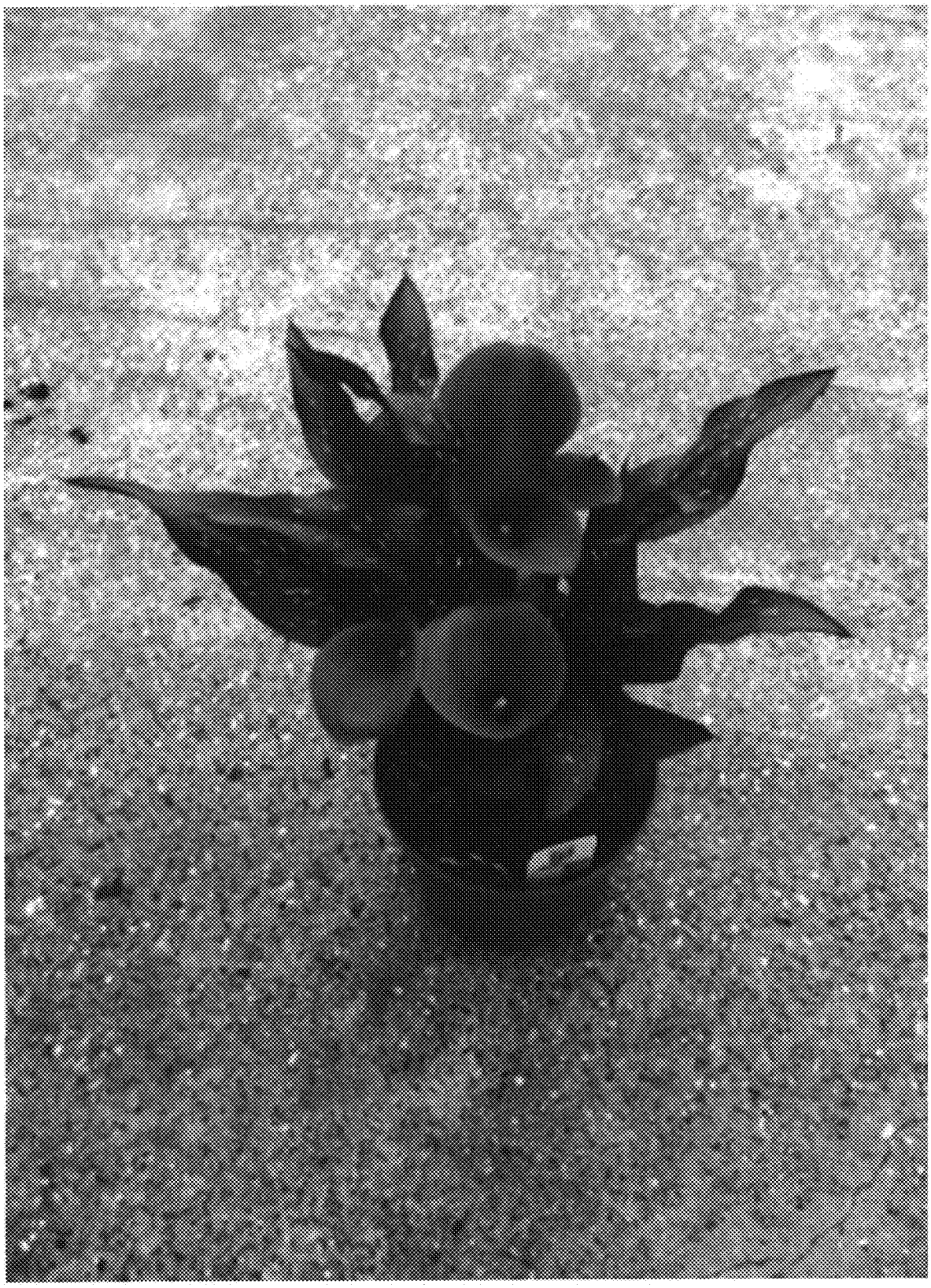
FIG. 1 illustrates a single flowering plant of the new variety.
Figure 2:
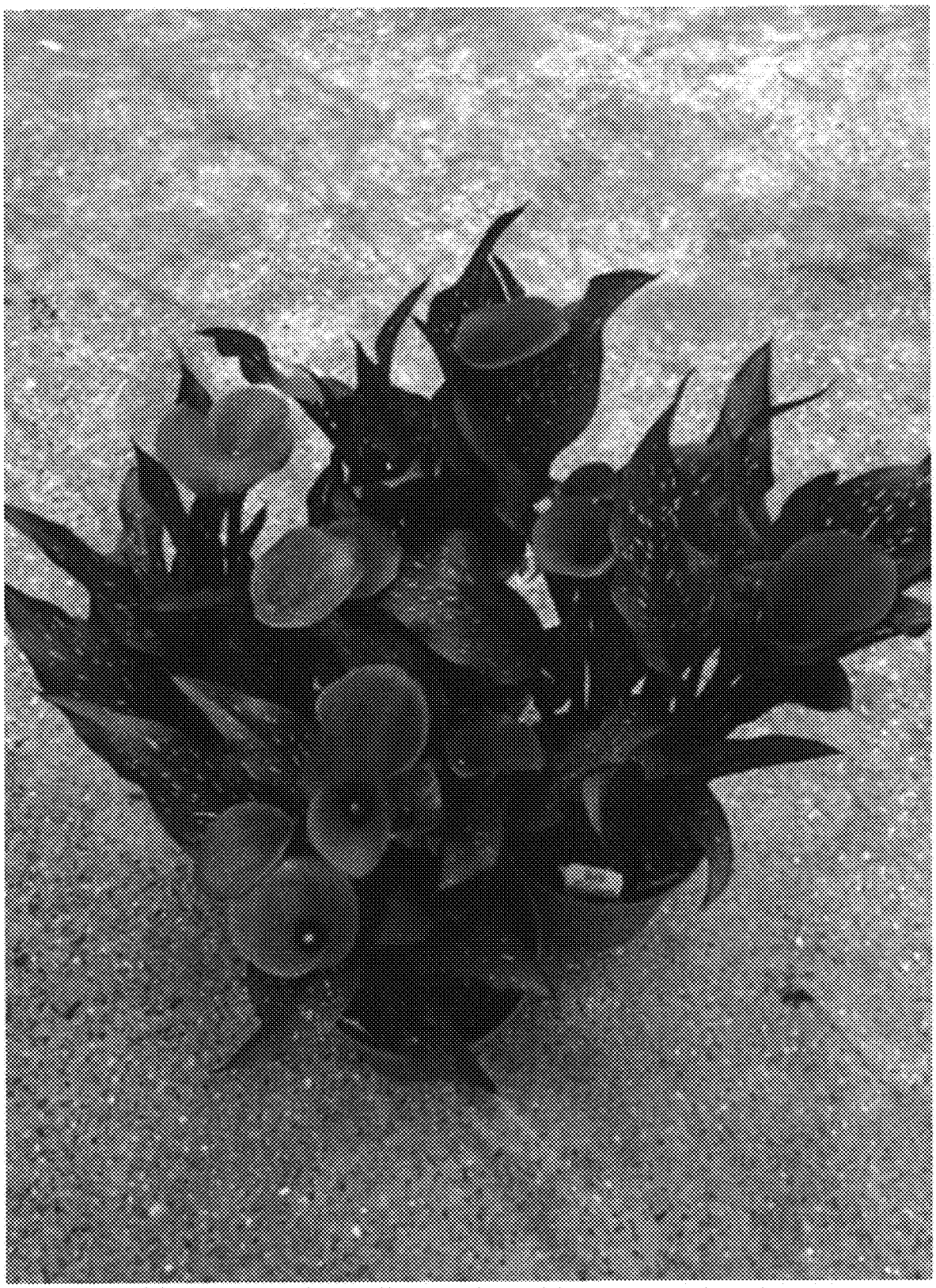
FIG. 2 illustrates multiple flowering plants of the new variety.

Type: Deciduous.

*Size*.—Height of the leaf canopy above the soil: 12-19 cm. Height of top of inflorescences above the soil: 22-25 cm. Diameter: 22-37 cm.

*Form*.—Semi-spreading.

*Number of inflorescences per tuber*.—Size 16-18 cm in diameter: 5-10 inflorescences.

*Branches*.—Number: Average. Color: Green Group RHS 143B to 143C. Young shoot color: Red-Purple Group RHS 59A to 59B.

Leaves:

*Size*.—Width: 6.5-8 cm, with the broadest part being slightly below the middle. Length: 18-21 cm.

*Number per plant*.—15-19.

*Leaf blade lobes*.—Absent.

*Shape*.—Lanceolate.

*Apex*.—Apiculate.

*Base*.—Attenuate.

*Margin*.—Entire; having a slight color of Red-Purple Group RHS 60A to 60B.

*Color*.—Upper surface: Green Group RHS 137B to 137C, with few to average, linear Greyed-White Group RHS 156A to 156B maculations present. Lower surface: Green Group RHS 143A to 143B, with few to average, linear Greyed-White Group RHS 156C to 156D maculations present.

*Veins*.—Configuration: Pinnate. Color (both surfaces): Greyed-Purple Group RHS N186D.

*Surface texture*.—Smooth (both surfaces).

*Petiole*.—Length: 12-19 cm. Diameter: 7-12 mm. Color: The base is Brown Group RHS 200B to 200C, the upper part is Purple Group RHS N77A.

*Roots*.—Color: White Group RHS 155C. Branching description: Fibrous root system. Several main roots emerge from the top of the tuber and form a small number of lateral roots.

Spathe:

*Size*.—Length (measured from opening to tip): 4.5-6.5 cm. Width: 4.5-5.5 cm. Height: 6-8 cm.

*Color* (*at all stages of maturity and fading*).—Throat spot: A medium area of Violet-Blue Group RHS N92B. Upper surface: Red-Purple Group RHS 59B to 59C. Lower surface: Red-Purple Group RHS 61A to 61B.

*Vein color*.—Red-Purple Group RHS 59A.

*Shape*.—Funnel.

*Apex*.—Apiculate.

*Base*.—Amplexicaul.

*Margin*.—Entire with very weak to weak recurving and a color of Red-Purple Group RHS 59C to 59D.

*Spadix*.—Shape: Cylinder. Size: Length: 22-30 mm. Diameter: 7-9 mm. Color: Yellow-grange Group RHS 15A to 15B. Position relative to spathe: Upright.

*Peduncle*.—Size: Length: 22-25 cm. Diameter: 8-11 mm. Color: The upper part is Greyed-Purple Group RHS 187A to 187B, the lower part is Brown Group RHS 200C to 200D. Texture: Smooth.

Reproductive organs:

*Location of female organs*.—Basal position of the spadix.

*Location of male organs*.—Upper position of the spadix.

*Perianth*.—Conspicuous.

*Stamens*.—Presence: Not visible before pollen release. Number: Between 480 and 600. Pollen amount: Scarce. Color: Between White Group RHS 155B and 155C.

*Anther*.—Shape: Round. Length: Less than 1 mm. Color: Yellow Group RHS 8B to 8C.

*Filament*.—Length: Less than 1 mm. Color: White Group RHS 155D.

*Pistils*.—Number: 15 to 30. Length beyond perianth: About 1 mm.

*Stigma*.—Shape: Round. Size: Less than 1 mm.

*Style*.—Length: Less than 1 mm. Color: Yellow Group RHS 8B to 8C.

*Ovaries*.—Texture: Smooth. Length: Between 1 to 10 mm. Width: Between 1 to 10 mm. Color: The top color is Yellow Group RHS 12B to 12C, the bottom color is Red-Purple Group RHS 58A.

Seeds:

*Length*.—2.7-3.4 mm.

*Width*.—2.5-2.9 mm.

*Color*.—Brown Group RHS 200B to 200C.

*Amount*.—35 per inflorescence.

Disease resistance: No unusual susceptibility/resistance to diseases noticed to date.

Pest resistance: No unusual susceptibility/resistance to pests noticed to date.

Heat tolerance: No heat tolerance.

Hardiness: Not tested to date.

Flowering: In general, the time from indoor and outdoor planting to first flowering takes about eight weeks in The Netherlands.

Lastingness: About two weeks on the plant.

Fragrance: None.

I claim:

1. A new and distinct variety of calla lily plant named 'Dozantoky' as herein described and illustrated.

* * * * *